US009322643B2

(12) United States Patent
Huang et al.

(10) Patent No.: US 9,322,643 B2
(45) Date of Patent: Apr. 26, 2016

(54) APPARATUS AND METHOD FOR 3D SURFACE MEASUREMENT

(71) Applicant: Nanyang Technological University, Singapore (SG)

(72) Inventors: Lei Huang, Singapore (SG); Chi Seng Ng, Singapore (SG); Hoe Jyh Koh, Singapore (SG); Anand Krishna Asundi, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 0 days.

(21) Appl. No.: 14/350,359

(22) PCT Filed: Oct. 17, 2012

(86) PCT No.: PCT/SG2012/000386
§ 371 (c)(1),
(2) Date: Apr. 7, 2014

(87) PCT Pub. No.: WO2013/058710
PCT Pub. Date: Apr. 25, 2013

(65) Prior Publication Data
US 2014/0253929 A1    Sep. 11, 2014

Related U.S. Application Data

(60) Provisional application No. 61/548,447, filed on Oct. 18, 2011.

(51) Int. Cl.
*G01B 11/24* (2006.01)
*G01B 11/25* (2006.01)
(Continued)

(52) U.S. Cl.
CPC .......... *G01B 11/2545* (2013.01); *G01B 11/245* (2013.01); *G01B 11/25* (2013.01); *G01N 21/8806* (2013.01); *G06T 7/0057* (2013.01); *G06T 7/0075* (2013.01)

(58) Field of Classification Search
CPC .... G01B 11/25; G01B 11/2545; G01B 11/24; G01B 11/30; G01N 21/86; G09G 5/10
USPC .................................................. 356/601–616
See application file for complete search history.

(56) References Cited

U.S. PATENT DOCUMENTS 4,871,256 A * 10/1989 Grindon .................. 356/610
5,085,502 A *  2/1992 Womack et al. ......... 356/605
(Continued)

FOREIGN PATENT DOCUMENTS

WO    2013058710 A1    4/2013

OTHER PUBLICATIONS

Foreign Communication from a Related Counterpart Application, International Search Report and Written Opinion dated Dec. 3, 2012, International Application No. PCT/SG12/00386 filed on Oct. 17, 2012.

(Continued)

*Primary Examiner* — Tarifur Chowdhury
*Assistant Examiner* — Isiaka Akanbi (57) ABSTRACT

An apparatus for 3D surface measurement of a target surface, the apparatus comprising: a first projector configured to project a fringe pattern onto the target surface; a second projector configured to project a fringe pattern onto the target surface; a first camera configured to capture the fringe patterns projected by the first projector and the second projector; a second camera configured to capture the fringe patterns projected by the first projector and the second projector; and a computer configured to perform fringe pattern processing of the fringe patterns captured by the first camera and the second camera and to perform data stitching and merging to obtain a 3D surface reconstruction.

7 Claims, 7 Drawing Sheets

(51) Int. Cl.
*G01B 11/245* (2006.01)
*G01N 21/88* (2006.01)
*G06T 7/00* (2006.01)

(56) References Cited

U.S. PATENT DOCUMENTS

| | | | | |
|---|---|---|---|---|
| 5,457,325 | A * | 10/1995 | Huberty | A43D 1/025 250/559.29 |
| 5,753,931 | A * | 5/1998 | Borchers | A43D 1/025 250/559.05 |
| 7,306,341 | B2 * | 12/2007 | Chang | 353/94 |
| 8,285,025 | B2 * | 10/2012 | Baldwin et al. | 382/141 |
| 2007/0195285 | A1 * | 8/2007 | Jaynes | G03B 37/04 353/69 |
| 2010/0092040 | A1 | 4/2010 | Fischer | |

OTHER PUBLICATIONS

Foreign Communication from a Related Counterpart Application, International Preliminary Report on Patentability dated Sep. 24, 2013, International Application No. PCT/SG12/00386 filed on Oct. 17, 2012.

Hu, Q., et al., "Calibration of a three-dimensional shape measurement system", Optical Engineering 2003, vol. 42, No. 2, pp. 478-493.

* cited by examiner

APPARATUS AND METHOD FOR 3D SURFACE MEASUREMENT

CROSS-REFERENCE TO RELATED APPLICATIONS

This application is a filing under 35 U.S.C. 371 as the National Stage of International Application No. PCT/SG2012/000386, filed Oct. 17, 2012, entitled "APPARATUS AND METHOD FOR 3D SURFACE MEASUREMENT", which claims the benefit of and priority to U.S. Provisional Patent Application No. 61/548,447, filed Oct. 18, 2011 and entitled "APPARATUS AND METHOD FOR 3D SURFACE MEASUREMENT", both of which are incorporated herein by reference in their entirety for all purposes.

TECHNICAL FIELD

This invention relates generally to an apparatus and method for three-dimensional (3D) surface measurement, and relates more particularly, though not exclusively, to an apparatus and method for three-dimensional (3D) surface measurement of a non-contactable object having steep profiles.

BACKGROUND

Fringe projection profilometry (FPP) is an optical method for measuring a 3D shape or surface of an object, with the advantages of having a full field, high speed and non-contact nature [3-6]. This technique utilizes a projector to project predefined images, which are usually fringe patterns, onto a target surface, and uses a camera to capture the reflected fringe patterns. It can be automatically controlled by computer, and recorded images are processed with algorithms to calculate some intermediate results such as phase values, modulation values, and height values. Output using FPP may be in the form of a cloud of 3D points, otherwise known as a "3D point cloud." A triangle mesh or surface drawings may be applied for better visualization. However, problems of shadow and obstruction issues arise when mechanical movement or rotation, either of the object to be measured or of the projector and camera, cannot or is preferred not to take place during measurement.

SUMMARY

An apparatus and method for 3D shape measurement is proposed that enables two projectors and two cameras to form four optical noncontact 3D shape sensors for shape measurement and inspection with enhancement of data density and validity. The four optical 3D sensors are located at positions surrounding a target surface so as to be able to obtain data of the target surface from four different views without any mechanical shifting or rotation required of either the target surface or the optical 3D sensors.

Calibration of all four optical 3D sensors is performed with a same world or global coordinates, which makes data combination and merging easy without requiring any additional feature points for capturing and identification.

A software provided for system control and data processing with high automaticity renders the apparatus and method especially user-friendly.

An algorithm of phase calculation with invalidity identification framework provides more reliable phase results for dimensional data calculation.

According to a first aspect, there is provided an apparatus for 3D surface measurement of a target surface, the apparatus comprising: a first projector configured to project a fringe pattern onto the target surface; a second projector configured to project a fringe pattern onto the target surface; a first camera configured to capture the fringe patterns projected by the first projector and the second projector; a second camera configured to capture the fringe patterns projected by the first projector and the second projector; and a computer configured to perform fringe pattern processing of the fringe patterns captured by the first camera and the second camera and to perform data stitching and merging to obtain a 3D surface reconstruction.

The first projector, the second projector, the first camera and the second camera may be calibrated with a same global coordinates.

The first projector and the first camera may form a first optical 3D sensor, the second projector and the first camera may form a second optical 3D sensor, the first projector and the second camera may form a third optical 3D sensor, and the second projector and the second camera may form a fourth optical 3D sensor.

The apparatus may further comprise a frame configured to support and position the first projector, the second projector, the first camera and the second camera over and around the target surface.

The first projector and the second projector may be positioned diametrically opposite each other about the target surface.

The first camera and the second camera may be positioned diametrically opposite each other about the target surface.

According to a second aspect, there is provided a method for 3D surface measurement of a target surface, the method comprising the steps of: a first projector projecting a fringe pattern onto the target surface; a first camera capturing the fringe pattern projected by the first projector; a second camera capturing the fringe pattern projected by the first projector; a second projector projecting a fringe pattern onto the target surface; the first camera capturing the fringe pattern projected by the second projector;

the second camera capturing the fringe pattern projected by the second projector; and a computer processing the captured fringe patterns and performing data stitching and merging to obtain a 3D surface reconstruction.

The method may further comprise calibrating the first projector, the second projector, the first camera and the second camera with a same global coordinates prior to the first projector projecting the fringe pattern onto the target surface.

Processing the captured fringe patterns may comprise performing phase retrieval and a phase invalidity identification process.

Performing data stitching and merging may comprise calculating an interval distance between two neighboring points obtained from processing the captured fringe patterns.

BRIEF DESCRIPTION OF THE DRAWINGS

In order that the invention may be fully understood and readily put into practical effect there shall now be described by way of non-limitative example only exemplary embodiments, the description being with reference to the accompanying illustrative drawings.

In the drawings:

FIG. 3b are images obtained by the combinations of FIG. 3a;

DETAILED DESCRIPTION OF EXEMPLARY EMBODIMENTS

An exemplary apparatus 10 and method (100) for 3D surface measurement will be described with reference to FIGS. 1 to 10 below.

Figure 1:
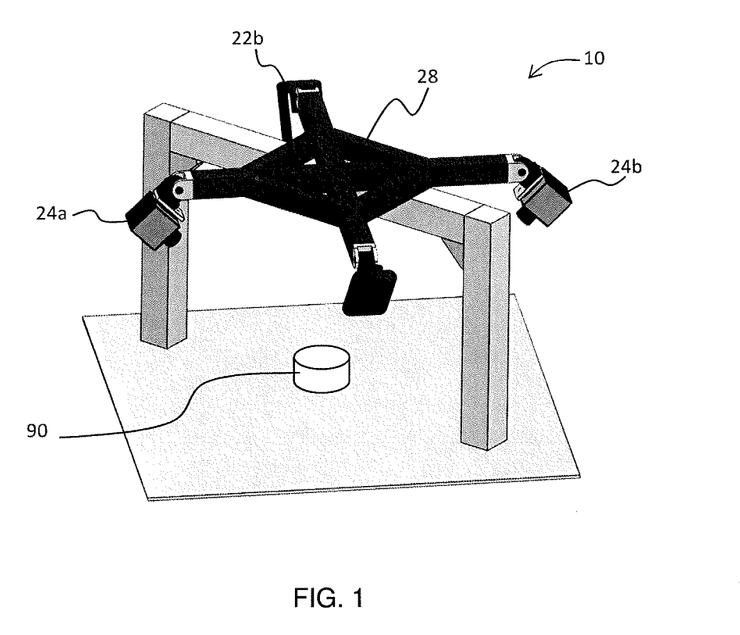
FIG. 1 is a schematic illustration of an apparatus for 3D surface measurement.
Figure 2:
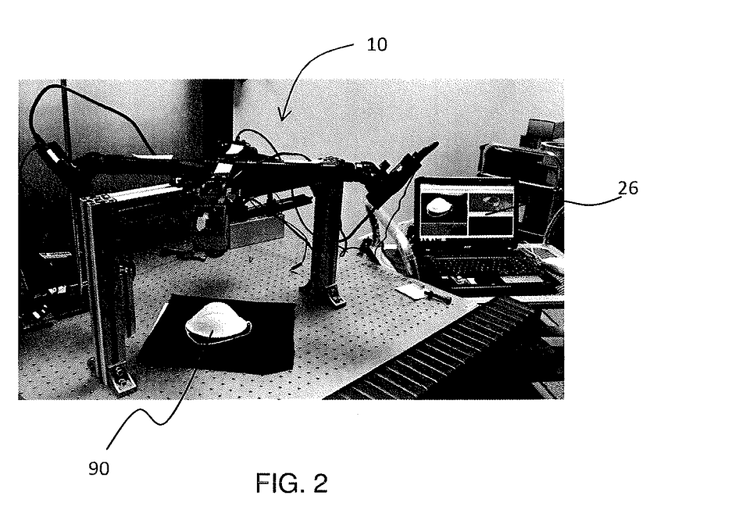
FIG. 2 is a photograph of the apparatus of FIG. 1.

As shown in FIGS. 1 and 2, the apparatus 10 comprises two projectors, a first projector 22a and a second projector 22b connected with a graphic processing unit which is able to expand a virtual computer screen. The projectors 22a, 22b each have a spatial light modulator (SLM) and are configured to project fringe patterns onto a target surface 90, serving as light sources for structured light illumination. The SLM is configured to modulate the intensity of the light beam projected by the projector 22a, 22b, and can modulate the phase or both intensity and phase simultaneously.

The apparatus 10 also comprises two cameras, a first camera 24a and a second camera 24b having appropriately chosen lenses. Connecting cables used may be either USB or FireWire wires. The cameras 24a, 24b each preferably have a digital photo sensor that may be a charge coupled device (CCD) or a complementary metal-oxide-semiconductor (CMOS) device, with a minimum a resolution of 1,024 by 1,280 pixels.

The projectors 22a, 22b and cameras 24a, 24b are positioned to surround the target surface 90, and are connected to a computer 26 with a display serving as a controlling and computing unit. The computer is used to control the projection and capture processes during measurement, and to process the captured images and dimensional data. The performance of each SLM is controlled by its control unit and the computer 26. The projectors 22a, 22b can thus be controlled to project any patterns generated by the computer 26. In this way, a phase shifting technique with temporal phase unwrapping technique can be readily implemented using these projectors 22a, 22b with no mechanical movement required of the target surface 90 or the projectors 22a, 22b and/or cameras 24a, 24b.

A frame 26 may be provided to support and position the projectors 22a, 22b and cameras 24a, 24b over and around the target surface 90. The frame 26 is preferably of a cruciform shape, with the projectors 22a, 22b and cameras 24a, 24b disposed separately at the end of each arm of the cruciform shape. In an exemplary embodiment, the two projectors 22a, 22b are disposed diametrically opposite each other about the target surface 90; likewise the two cameras 24a, 24b are disposed diametrically opposite each other about the target surface 90. The frame 26 is preferably configured to allow adjustment of the relative positions of the projectors 22a, 22b and cameras 24a, 24b in order to achieve a best configuration for working the apparatus 10.

Figure 3A:
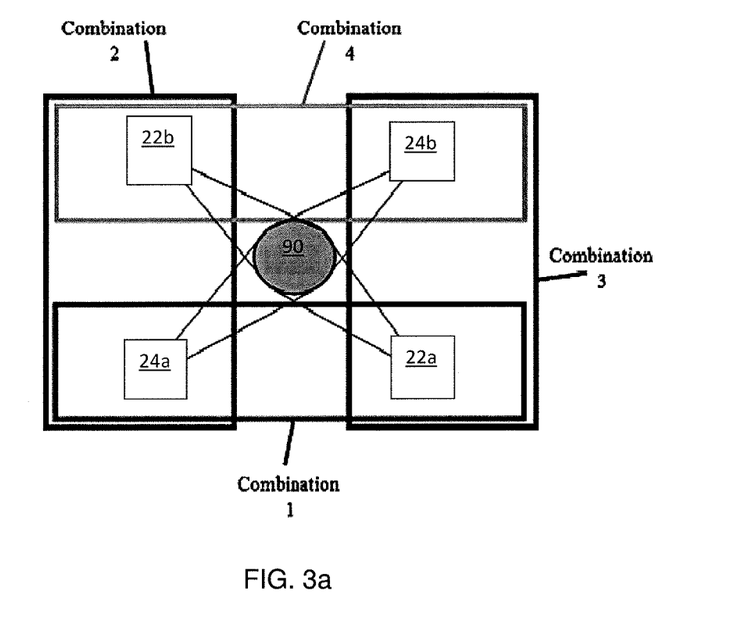
FIG. 3a is a schematic illustration of projector and camera combinations provided to solve shadow and obstruction problems.

Using the apparatus 10, a method (100) for true 3D shape measurement of surface with fringe projection without mechanical movement is achieved, while solving the shadow and obstruction issues. In the present method (100), the two projectors 22a, 22b and two cameras 24a, 24b are able to form four distinct optical 3D sensors using a combination of any one projector 22a or 22b and one camera 24a or 24b as shown in FIG. 3. The four optical 3D sensors thus comprise the following four combinations of projectors and cameras:

Combination 1: projector 22a with camera 24a;
Combination 2: projector 22b with camera 24a;
Combination 3: projector 22a with camera 24b; and
Combination 4: projector 22b with camera 24b.

With control by the computer 26, fringe patterns can be projected by each of the projectors 22a or 22b to let each of the cameras capture 24a or 24b the deformed fringe patterns which contain dimensional information of the tested or target surface 90. Because each of the four combinations of optical 3D sensor is located at a different viewing position, each combination thus gives a 3D point cloud from a different view. The whole surface shape of the target surface 90 without shadow and obstruction problems can thus be obtained by combining the four 3D point clouds obtained from the four different views by the four combinations of optical 3D sensors. All these processes are preferably configured to be done automatically with the computer 26 performing the controlling and numerical calculations.

Fringe Pattern Projection and Capture

Figure 10:
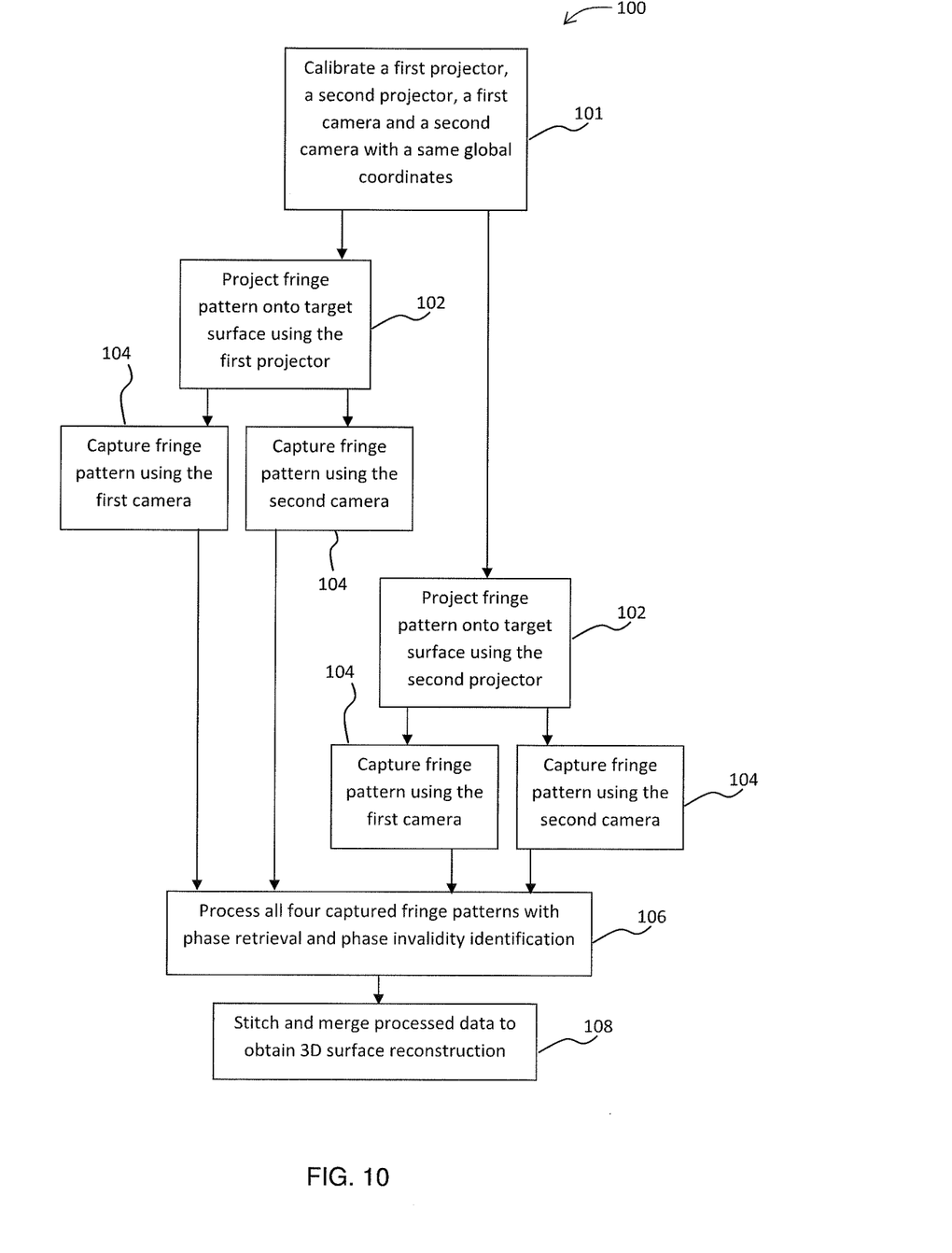
FIG. 10. is a flowchart of an exemplary method for 3D surface measurement.

In the present method (100), each combination 1, 2, 3 and 4 of the optical 3D sensor performs fringe projection profilometry in which a fringe pattern is sequentially projected onto the test object or target surface 90 (102) using each of the projectors 22a or 22b. The projected pattern in this process is preferably predefined. In the present method (100), multi-frequency sinusoidal fringe patterns with phase stepping are preferred as they can be easily implemented by the digital projectors 22a, 22b and processed with phase shifting and unwrapping algorithms for phase retrieval subsequently.

In an exemplary embodiment of the method (100), the fringe pattern used is a sinusoidal fringe, which is usually designed as $$f = 255 \times (0.5 + 0.5 \cos \phi) \quad (1)$$

Normally, the phase $\phi$ is linearly distributed along one direction.

Figure 3B:
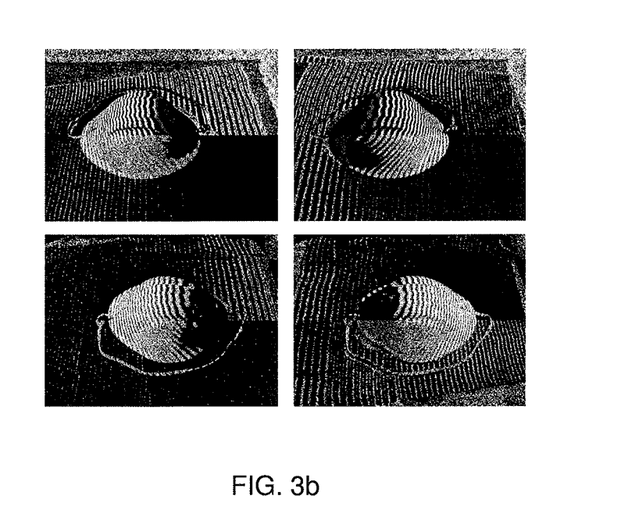
Figure 4A:
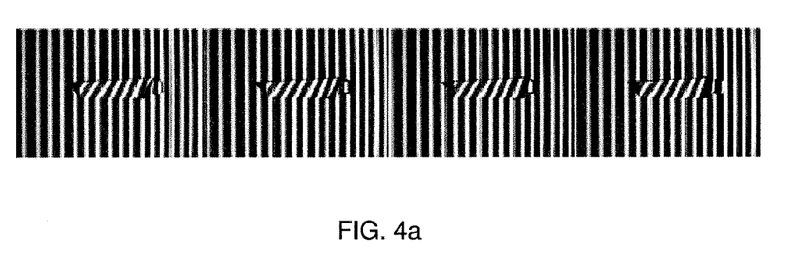
FIG. 4a are phase shifted fringe patterns.

From a camera view, the projected fringe pattern will seem to be deformed according to height variation of the tested or target surface 90. The fringe pattern projected by each projector 22a, 22b is separately captured by each of the cameras 24a, 24b (104), and the captured fringe patterns as shown in FIG. 3b are stored in the computer 26. Since all four combinations of the optical 3D sensors perform the fringe projection profilometry, four different fringe patterns are captured. FIG. 4a is another example of four captured images of a same target surface obtained using the apparatus 10.

Generally the captured fringe intensity I can be expressed as $$I = A + B \cos \phi, \quad (2)$$

where A is the background intensity and B is the amplitude of the sinusoidal fringe.

Phase Retrieval with Invalidity Identification Framework

Digital image processing then follows, but since the fringe pattern is a special type of image, usually the procedure is called fringe pattern processing or phase retrieval (106). The captured fringe patterns are phase shifted phase patterns as shown in FIG. 4a, and are used as input data for a phase shifting algorithm to calculate fringe phase and modulation.

Figure 4B:
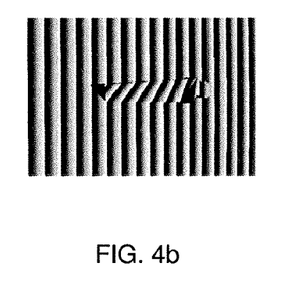
FIG. 4b is a retrieved wrapped phase map.

For phase retrieval, once the phase shifting technique is utilized to obtain a retrieved wrapped phase map as shown in FIG. 4b, the nth phase shifted fringe patterns $I_n$ could be represented by the following equation (3):

$$I_n = A + B \cos(\phi + \delta_n), \quad (3)$$

where the phase shifting amount is calculated by equation (4)

$$\delta_n = 2\pi \frac{n}{N}, \quad (4)$$
$$n = 0, 1, 2, \ldots, N-1,$$

and N is the total phase shifting number.

The phase shifting algorithm can be applied for wrapped phase retrieval. The fringe phase result of each fringe frequency is used together to unwrap phase wraps, which limits the phase value to within [−pi, pi] due to an arctangent operation.

Using a least squares fitting of phase shifting and temporal phase unwrapping process, not only can the phase be unwrapped, but phase validity can be also identified. The wrapped phase $\phi^w$ and fringe modulation M can be calculated by the following equations (5) and (6):

$$\phi^w = -\arctan \frac{\sum_{n=0}^{N-1} I_n \sin\delta_n}{\sum_{n=0}^{N-1} I_n \cos\delta_n}, \quad (5)$$

$$M = \frac{2}{N} \sqrt{\left(\sum_{n=0}^{N-1} I_n \sin\delta_n\right)^2 + \left(\sum_{n=0}^{N-1} I_n \cos\delta_n\right)^2} \quad (6)$$

Furthermore, the wrapped phase map as shown in FIG. 4b will be unwrapped by using temporal phase unwrapping technique if the multi-frequency fringe patterns are designed and projected.

The least squares fitting of the unwrapped phase with different fringe frequencies from temporal phase unwrapping will improve the phase measuring precision and at the same time it can also provide Root Mean Square Error (RMSE) as a judging quantity for identification of invalid phase points. A common temporal phase unwrapping procedure is given by the following equation (7):

$$\phi_k^u = \begin{cases} \phi_k^w, & k = 1 \\ \phi_k^w + \text{Round}\left(\frac{\phi_{k-1}^u \cdot m_k / m_{k-1} - \phi_k^w}{2\pi}\right) \cdot 2\pi, & k > 1 \end{cases}, \quad (7)$$

and RMSE can be calculated by the following equation (8):

$$RMSE = \sqrt{\frac{\sum_{k=1}^{K}(\phi_k^u - m_k \cdot X)^2}{K}} = \sqrt{\frac{\sum_{k=1}^{K}\left(\phi_k^u - m_k \cdot \sum_{k=1}^{K}\phi_k^u m_k / \sum_{k=1}^{K} m_k^2\right)^2}{K}}. \quad (8)$$

Figure 5:
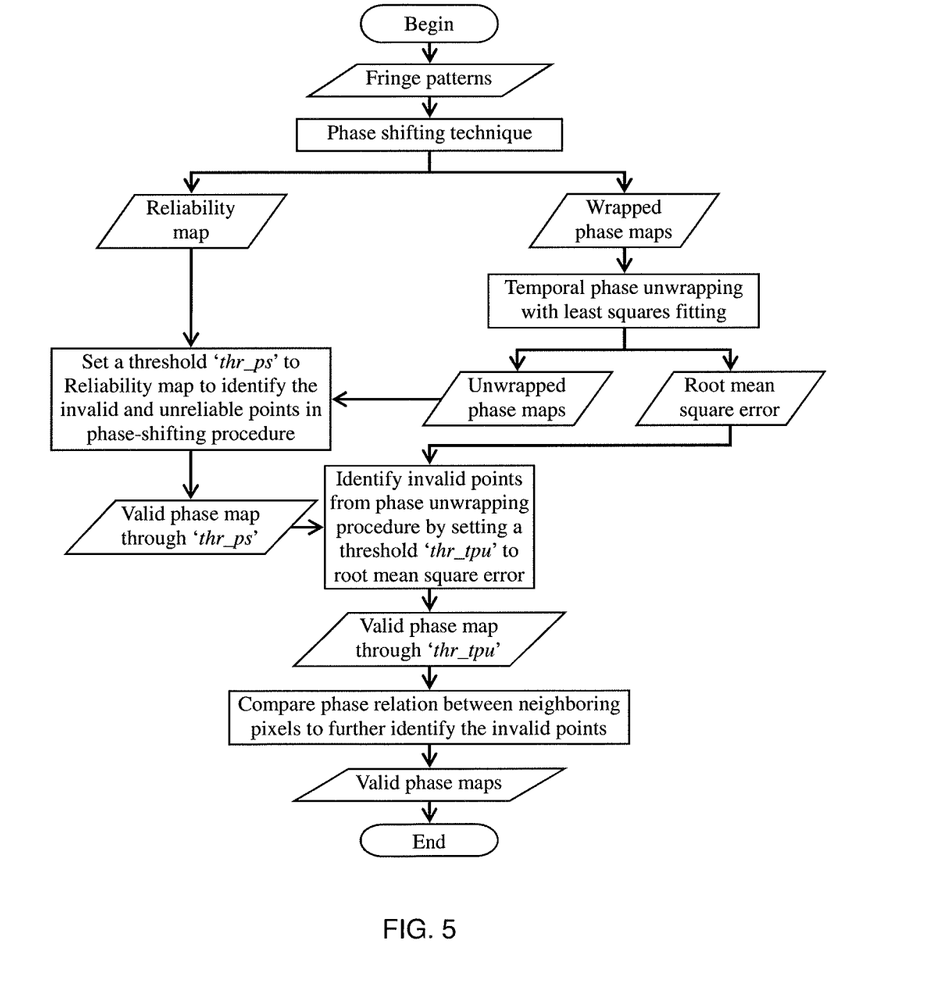
FIG. 5 is a flowchart of a phase invalidity identification method.

Using fringe modulation M and fitting error RMSE, the invalid phase values can be easily identified to improve the reliability of the phase dataset. The whole framework is shown in FIG. 5. Using the phase invalidity identification method or framework of FIG. 5 can significantly improve the reliability of phase values as well as the 3D point clouds, since the phase invalidity identification process is to make sure all phase values that will be processed in subsequent dimensional calculations are accurate and reliable.

System Calibration with Global Coordinates

Before actual measurement using the four combinations of optical 3D sensors is performed, calibration of the system or apparatus 10 should be carried out in advance (101). Calibration (101) of the apparatus 10 is different from conventional calibration approaches of fringe projection profilometry because a same coordinate of calibration for the multiple optical 3D sensors is required in order to make a dimensional dataset from every combination 1, 2, 3 and 4 of optical 3D sensor have the same world or global coordinates.

Figure 6:
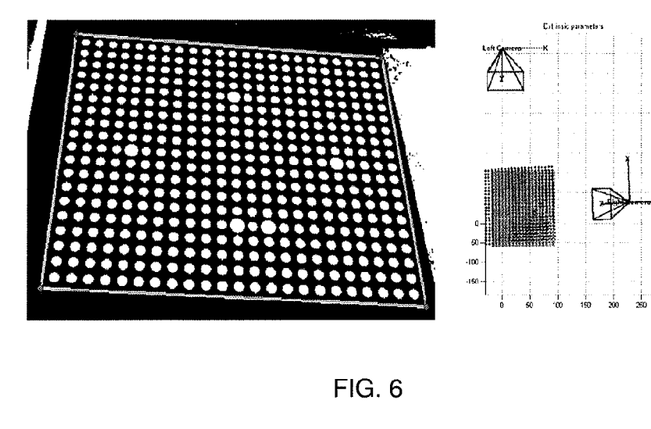
FIG. 6 is an illustration of calibration using a stereovision method taking into account camera and projector lens distortion.

During calibration (101), as shown in FIG. 6, a camera calibration pattern is presented at different positions and angles within a measuring range of the apparatus 10. A stereovision calibration method is then applied to each camera 24a or 24b and projector 22a or 22b combination 1, 2, 3 and 4 by treating the projector 22a or 22b as a camera according to the fringe phase values. To do so, the calibration pattern is located at a common position where every projector 22a, 22b and camera 24a, 24b can actually 'see' the whole calibration pattern. In this way, common or global coordinates can be determined and the whole calibration is based on these global coordinates.

Calibration (101) is essential for this apparatus 10 and method (100). The four optical 3D sensors 1, 2, 3, 4 should be calibrated with the same global coordinates in order to make data stitching in measurement more convenient. From the phase value, 3D data can be reconstructed once the apparatus 10 is calibrated. Ultimately, four sets of dimensional data from the four different views obtained by the four combinations 1, 2, 3 and 4 of optical 3D sensors are stitched and merged into one dataset (108).

Dimensional Reconstruction with Data Stitching and Merging

Figure 7:
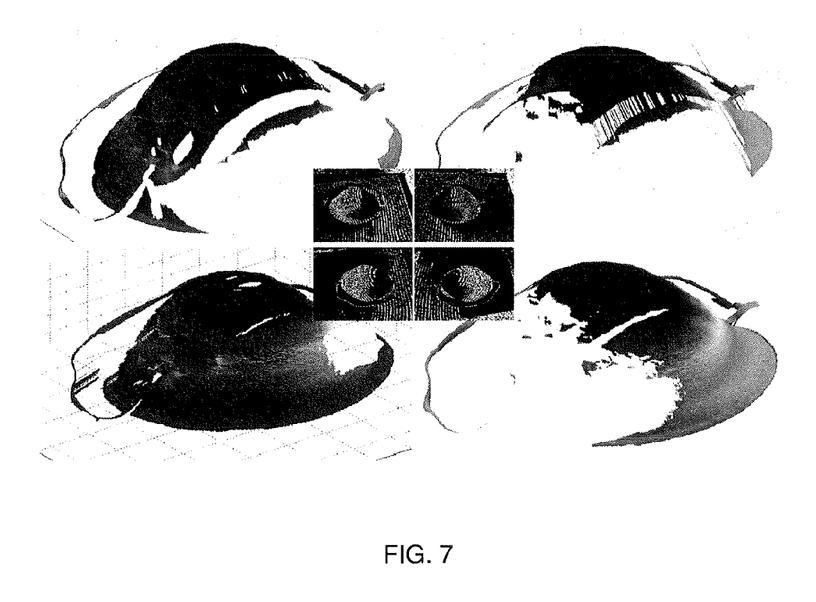
FIG. 7 is a collection of different views of a reconstructed 3D surface.
Figure 8:
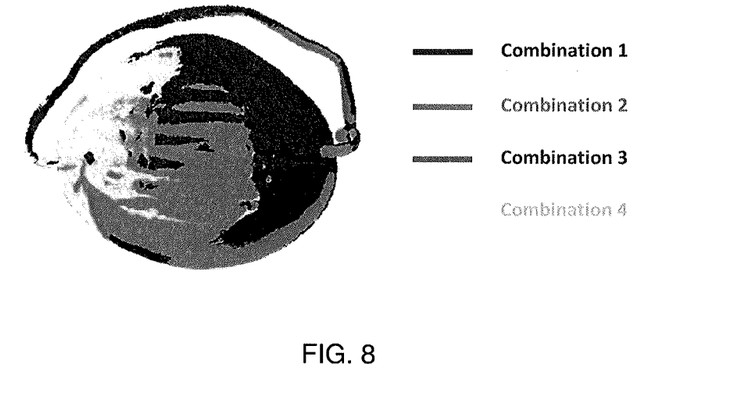
FIG. 8 is an illustration of data registration of a 3D surface.
Figure 9:
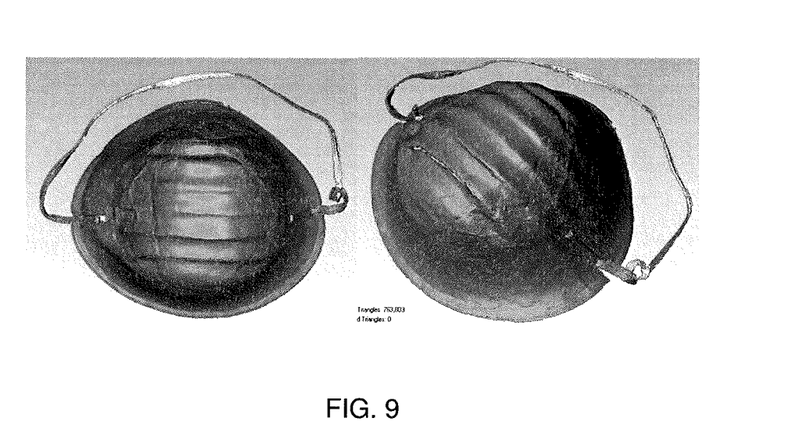
FIG. 9 is a data visualization of a 3D surface in triangle surfaces with lighting.

Once the system is calibrated, the relationship between phase value and dimensional value is already determined. That is to say, in measurement, if a reliable phase value can be retrieved from the fringe patterns, the out-of-plane and in-plane dimensions can be easily reconstructed with system parameters obtained from calibration. For each combination 1, 2, 3, or 4 of projector 22a or 22b and camera 24a or 24b, the resultant data is one set of dimensional data. In all, the method (100) reconstructs four dimensional datasets as shown in FIG. 7, each dataset comprising a 3D point cloud. Subsequently, these are combined with merging of some data at the common regions if the 3D point cloud is too dense, which is not always good for later processing such as data visualization. As mentioned above, the four datasets are located in the same global coordinates, as determined during the calibration (101) described above. Therefore, data stitching (108) is relatively easily performed, as shown in FIG. 8. The data stitching or merging process (108) is implemented by calculating an interval distance between two neighboring points in order to remove some too dense points. The resultant 3D point cloud is friendly for following or subsequent processing, if any is desired. For example, as shown in FIG. 9, the 3D data can be nicely visualized with triangle surfaces and lighting.

It is envisaged that the above described apparatus 10 and method (100) may be adapted to many production lines for online inspection of produced parts. The apparatus 10 may be adjusted to change the measuring volume for different applications where necessary.

Whilst there has been described in the foregoing description exemplary embodiments of the present invention, it will be understood by those skilled in the technology concerned that many variations in details of design, construction and/or operation may be made without departing from the present invention. For example, while two projectors and two cameras have been described above, the apparatus may comprise more than two projectors and more than two cameras for more robust 3D surface measurement.

The invention claimed is:

1. An apparatus for 3D surface measurement of a target surface, the apparatus comprising:
   only two projectors, the two projectors comprising, a first projector configured to project a fringe pattern onto the target surface and;
   a second projector configured to project a fringe pattern onto the target surface;
   only two cameras, the two cameras comprising, a first camera configured to capture the fringe patterns projected by the first projector and the second projector and;
   a second camera configured to capture the fringe patterns projected by the first projector and the second projector;
   wherein the first projector, the second projector, the first camera and the second camera are calibrated with a same global coordinates,
   wherein the first projector and the first camera form a first optical 3D sensor configured to capture a first fringe pattern, wherein the second projector and the first camera form a second optical 3D sensor configured to capture a second fringe pattern, wherein the first projector and the second camera form a third optical 3D sensor configured to capture a third fringe pattern, and wherein the second projector and the second camera form a fourth optical 3D sensor configured to capture a fourth fringe pattern; and
   a computer configured to:
      perform fringe pattern processing of the first fringe pattern to generate a first 3D point cloud,
      perform fringe pattern processing of the second fringe pattern to generate a second 3D point cloud,
      perform fringe pattern processing of the third fringe pattern to generate a third 3D point cloud,
      perform fringe pattern processing of the fourth fringe pattern to generate a fourth 3D point cloud, and
      perform data stitching and merging of the first 3D point cloud, the second 3D point cloud, the third 3D point cloud, and the fourth 3D point cloud to obtain a 3D surface reconstruction using the calibration with the same global coordinates.

2. The apparatus of claim 1, further comprising a frame configured to support and position the first projector, the second projector, the first camera and the second camera over and around the target surface.

3. The apparatus of claim 1, wherein the first projector and the second projector are positioned diametrically opposite each other about the target surface.

4. The apparatus of claim 1, wherein the first camera and the second camera are positioned diametrically opposite each other about the target surface.

5. A method for 3D surface measurement of a target surface, the method comprising the steps of:
   a first projector, of only two projectors, projecting a fringe pattern onto the target surface;
   a first camera, of only two cameras, capturing a first fringe pattern projected by the first projector;
   a second camera, of the only two cameras, capturing a second fringe pattern projected by the first projector;
   a second projector projecting a fringe pattern onto the target surface;
   the first camera capturing a third fringe pattern projected by the second projector;
   the second camera capturing a fourth fringe pattern projected by the second projector;
   wherein the first projector and the first camera form a first optical 3D sensor, wherein the second projector and the first camera form a second optical 3D sensor, wherein the first projector and the second camera form a third optical 3D sensor, and wherein the second projector and the second camera form a fourth optical 3D sensor;
   a computer processing the captured fringe patterns and performing data stitching and merging to obtain a 3D surface reconstruction, wherein processing the captured fringe patterns comprises processing the first fringe pattern to generate a first 3D point cloud, processing the second fringe pattern to generate a second 3D point cloud, processing the third fringe pattern to generate a third 3D point cloud, and processing the fourth fringe pattern to generate a fourth 3D point cloud; and
   calibrating the first projector, the second projector, the first camera and the second camera with a same global coordinates prior to the first projector projecting the fringe pattern onto the target surface.

6. The method of claim 5, wherein processing the captured fringe patterns comprises performing phase retrieval and a phase invalidity identification process.

7. The method of claim 5, wherein performing data stitching and merging comprises calculating an interval distance between two neighboring points obtained from processing the captured fringe patterns.

* * * * *